(12) United States Patent
Gupta et al.

(10) Patent No.: US 8,669,061 B2
(45) Date of Patent: Mar. 11, 2014

(54) METHOD FOR THE PREVENTION OF CARRYOVER CONTAMINATION IN NUCLEIC ACID AMPLIFICATION TECHNOLOGIES

(75) Inventors: Amar Gupta, Danville, CA (US); Stephen Gordon Will, Oakland, CA (US); Roy Bohenzky, Mountain View, CA (US); Janine Montiel, Fremont, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 620 days.

(21) Appl. No.: 12/485,569

(22) Filed: Jun. 16, 2009

(65) Prior Publication Data
US 2010/0093041 A1 Apr. 15, 2010

Related U.S. Application Data

(60) Provisional application No. 61/076,111, filed on Jun. 26, 2008.

(51) Int. Cl.
*C12P 19/34* (2006.01)

(52) U.S. Cl.
USPC .......................... 435/6.12; 435/91.2

(58) Field of Classification Search
None
See application file for complete search history.

(56) References Cited

U.S. PATENT DOCUMENTS

| | | | |
|---|---|---|---|
| 6,287,823 | B1 | 9/2001 | Hartley |
| 6,413,747 | B1 | 7/2002 | Kato et al. |
| 6,518,026 | B2 | 2/2003 | Hartley |
| 2002/0072095 | A1 | 6/2002 | Hartley et al. |
| 2003/0077637 | A1 | 4/2003 | Hartley et al. |
| 2010/0022403 | A1* | 1/2010 | Kurn et al. ............... 506/9 |

FOREIGN PATENT DOCUMENTS

| | | | |
|---|---|---|---|
| EP | 1038974 | A1 | 9/2000 |
| EP | 1041159 | A2 | 10/2000 |
| EP | 1041159 | A3 | 10/2000 |
| EP | 09008229 | | 10/2009 |
| JP | 6277061 | A | 10/1994 |
| JP | 8009997 | A | 1/1996 |
| JP | 11113573 | A | 4/1999 |
| JP | 2001008680 | A | 1/2001 |
| WO | 9712061 | A1 | 4/1997 |
| WO | 02090536 | A2 | 11/2002 |
| WO | 02090536 | A3 | 11/2002 |

OTHER PUBLICATIONS

Ahokas, H. and Erkkila, M. J., 1993, "Interference of PCR amplification by the polyamines, spermine and spermidine", Genome Research, 3:65-68.
Kleiboeker, Steven B., 2005, "Quantitative assessment of the effect of uracil-DNA glycosylase on amplicon DNA degradation and RNA amplification in reverse transcription-PCR", Virology Journal, 2:29.
Kobayashi, Atsushi, et al., 2005, "Novel PCR-mediated mutagenesis employing DNA containing a natural abasic site as a template and translesional Taq DNA polymerase", Journal of Biotechnology, 116:227-232.
Longo, Mary C., et al., 1990, "Use of uracil DNA glycosylase to control carry-over contamination in polymerase chain reactions", Gene, 93:125-128.
Sikorsky, Jan A., et al., 2007, "DNA damage reduces Taq DNA polymerase fidelity and PCR amplification efficiency", 355:431-437.
Steullet, Vera, et al., 1999, "Cleavage of Abasic Sites in DNA by Intercalator-amines", Bioorganic & Medicinal Chemistry, 7:2531-2540.
Bailly, Veronique, et al., 1989, "The multiple activities of *Escherichia coli* endonuclease IV and the extreme labiltiy of 5'-terminal base-free deoxyribose 5-phosphates", Biochimie Journal., 259:761-768.
Hitomi, Kenichi, et al., 2007, "The intricate structural chemistry of base excision repair machinery: Implications for DNA damage recognition, removal, and repair", DNA Repair, 6(4):410-428.
Kleiboeker, Steven B., 2005, "Quantitative assessment of the effect of uracil-DNA glycosylase on amplicon DNA degradation and RNA amplification in reverse transcription-PCR", Virology Journal, 2(1):29.
Longo, Mary C., et al., 1990, "Use of uracil DNA glycosylase to control carry-over contamination in polymerase chain reactions" Gene, 93(1):125-128.
McHugh, Peter J., et al., 1995, "Novel reagents for chemical cleavage at abasic sites and UV photoproducts in DNA", Nucleic Acids Research, 23(10):1664-1670.
Steullet, Vera, et al., 1999, "Cleavage of Abasic Sites in DNA Intercalator-amines", Bioorganic & Medicinal Chemistry, 7(11):2531-2540.
Thornton, Charles G., et al., 1992, "Utilizing Uracil DNA Glycosylase to Control Carryover Contamination in PCR: Characterization of Residual UDG Activity Following Thermal Cycling", BioTechniques, 13(2):180-184.
Williams, Marshall, et al., 1990, "A Mollicute (Mycoplasma) DNA Repair Enzyme: Purification and Characterization of Uracil-DNA Glycosylase", Journal of Bacteriology, 172(6):2979-2985.

\* cited by examiner

*Primary Examiner* — Gary Benzion
*Assistant Examiner* — David Thomas
(74) *Attorney, Agent, or Firm* — David J. Chang; Olga Kay (57) ABSTRACT

An improved method of preventing carryover contamination of an amplification reaction involves treating uracil-containing DNA with uracil-N-DNA glycosylase and heating the DNA in the presence of polyamines, such as spermidine, spermine and the like. Alternatively, after treatment with uracil-N-DNA glycosylase, the reaction is further incubated with an enzyme having AP lyase activity.

6 Claims, 9 Drawing Sheets

NTC: No Template Control

SEQUENCE LISTING

<160> NUMBER OF SEQ ID NOS: 1

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
tttgcatggc tgcutgatgt cccccccact                              29

METHOD FOR THE PREVENTION OF CARRYOVER CONTAMINATION IN NUCLEIC ACID AMPLIFICATION TECHNOLOGIES

SEQUENCE LISTING

The instant application contains a Sequence Listing which has been submitted via EFS-Web and is hereby incorporated by reference in its entirety. Said ASCII copy, created on Dec. 7, 2009, is named 24623US1.txt, and is 729 bytes in size.

FIELD OF THE INVENTION

The invention relates generally to the methods of nucleic acid amplification and more specifically, to the control of carryover contamination during amplification of nucleic acids.

BACKGROUND OF THE INVENTION

Polymerase Chain Reaction (PCR) enables specific amplification of as little as a single copy of a target nucleic acid sequence. High sensitivity and specificity of PCR proved to be of great value in diagnostics, forensics and other applications where a small amount of target nucleic acid must be detected. Unfortunately, the same high sensitivity of PCR assays makes them vulnerable to contamination and false positive results. In forensics and disease screening (such as HIV testing), false positive results can have devastating consequences.

The most common source of false positive results is "carryover contamination", where a PCR product (amplicon) from a prior assay contaminates subsequent PCR assays. The contaminant may be transmitted by a technician, an instrument or even via aerosol. In a "negative" sample, where the target nucleic acid is absent, the contaminant creates a false positive result. In a "positive" sample, where the target nucleic acid is present, the contaminant is co-amplified with the true target. Such co-amplification may distort a result of a quantitative assay, where exact amount of the true target must be determined.

A popular and effective way of preventing carryover contamination involves the use of uracil DNA glycosylases, specifically UNG (EC 3.2.2.3). These enzymes recognize uracils present in single-stranded or double-stranded DNA and cleave the N-glycosidic bond between the uracil base and the deoxyribose, leaving an abasic site. See e.g. U.S. Pat. No. 6,713,294. Uracil-DNA glycosylases, abbreviated as "UDG" or "UNG" include mitochondrial UNG1, nuclear UNG2, SMUG1 (single strand-selective uracil-DNA glycosylase), TDG (TU mismatch DNA glycosylase), MBD4 (uracil-DNA glycosylase with a methyl binding domain) and other eukaryotic and prokaryotic enzymes (See Krokan H. E. et al. "Uracil in DNA—occurrence, consequences and repair", Oncogene (2002) 21:8935-9232).

Uracil-DNA glycosylases are DNA repair enzymes that prevent among others, G to A transition mutations caused by deamination of cytosine into uracil. If cytosine (C) is deaminated into a uracil (U) and the DNA undergoes replication, an A would be incorporated opposite the U, where G was previously located opposite the C. If the uracil base is excised by the glycosylase prior to replication, the abasic site is repaired by short-patch or long-patch DNA repair pathway, involving endonuclease and DNA polymerase activities. In addition to DNA damage repair, DNA glycosylase activity plays a role in somatic mutation, including immunoglobulin class switch and somatic hypermutation during antibody affinity maturation. See Bransteitter R. et al. "First AID (Activation-induced cytidine deaminase) is needed to produce high affinity isotype-switched antibodies", J. Bio. Chem. (2007) 281:16833-16836.

Preparation of uracil-N-DNA glycosylase (UNG) optimized for the control of carryover contamination in amplification reactions has been disclosed for example, in the U.S. Pat. No. 6,187,575. The use of UNG to prevent carryover contamination has also been described. See Longo et al. "Use of uracil DNA glycosylase to control carry-over contamination in polymerase chain reaction" (1990) Gene, 93:125-128. State of the art method of controlling carryover contamination using UNG is described in U.S. Pat. Nos. 6,287,823 and 6,518,026 and U.S. Pub. No. 2003/0077637.

Generally, the method involves two steps. First, the PCR assays must include dUTP, so that the amplicons, which are potential carryover contaminants, contain uracil. The method involves substituting dUTP for some or all of the dTTP in the amplification reaction. Alternatively (or in addition), one or more uracils may be incorporated into the amplification primers. It should be noted, however, that if a uracil in the primer is too close to the 5'-end, the method is less efficient at preventing subsequent amplification. The use of dUTP does not interfere with PCR assays. After a uracil-containing amplicon is generated, it can be detected and analyzed by standard methods despite the presence of uracil in place of thymine.

Next, uracil-N-DNA glycosylase is added to a subsequent PCR. Conveniently, UNG is active in a standard reaction mixture that contains all the components of PCR. This enables adding UNG to assembled PCR reactions or even to the PCR master mix. Before the start of thermal cycling, the reaction mixture is incubated at a temperature optimal for the UNG activity within the context of the PCR master mix (about 50° C.) or within the temperature range where UNG is active. If a uracil-containing contaminant from a prior reaction is present, UNG will cleave off the uracil, leaving an abasic site. DNA with abasic sites is known to be labile at high temperature under high pH conditions. When the thermal cycling begins, such DNA is degraded. The high temperature also inactivates the UNG enzyme, allowing to generate new DNA amplicons containing uracil.

After treatment with UNG, abasic DNA must be efficiently cleaved at the abasic sites. Unless it is cleaved, abasic DNA becomes a template for the polymerase in subsequent amplification. For example, Taq DNA polymerase is known to bypass abasic sites by incorporating an adenosine opposite the missing base. A single bypass by the polymerase generates a perfect template for subsequent amplification (see Sikorsky, J. A. et al., "DNA damage reduces Taq polymerase fidelity and PCR amplification efficiency", Biochem. Biophys. Res. Commun. (2007) 355:431-437 or Kobayashi, A. et al. "Novel PCR-mediated mutagenesis employing DNA containing a natural abasic site as a template and translesional Taq DNA polymerase", J. Biotech. (2005) 116:227-232). Therefore the ability to efficiently cleave DNA at the abasic sites is essential for the overall success of the UNG-based method of preventing carryover contamination.

SUMMARY OF THE INVENTION

The present invention involves a method of improved carryover contamination control using a DNA glycosylase. Inventors have determined that the limiting factor in successful elimination of the carryover contaminant is efficient degradation of the abasic DNA. The accepted views are that the limiting step is the enzymatic digestion to generate abasic DNA. The subsequent step of non-enzymatic degradation of abasic DNA was believed to be simple, efficient and not needing improvement. The prior efforts to improve contamination control methods focused on adding more glycosylase enzyme for increasing incubation times. The inventors discovered that contrary to the accepted views, the enzymatic step is extremely efficient. At the same time, the non-enzymatic degradation step is inefficient and thus the likely source of persistent contamination. If a contaminant escapes degradation during the initial cycles of PCR, it is copied by the polymerase and can no longer be eliminated.

Inventors discovered that contamination control can be dramatically improved by providing agents that degrade or facilitate degradation of the abasic DNA in a sample. The most useful of such agents are those compatible with subsequent amplification. In some examples, the sample is contacted with polyamines. In some embodiments the polyamine is spermidine, spermine or an intercalator amine. At high temperatures and high pH, polyamines significantly improve degradation of the abasic DNA without inhibiting PCR. In other embodiments, the sample is contacted with an enzyme, catalyzing cleavage of the backbone of abasic DNA. The compositions and methods using these and similar agents are disclosed.

BRIEF DESCRIPTION OF THE DRAWINGS

FIG. 1A shows degradation at 50° C. FIG. 1B shows degradation at 50° C. followed by a 2 minute heat spike at 95° C.

FIG. 2A shows the amplification of various numbers of input copies of HCV DNA with or without 100 µM spermine. FIG. 2B shows the amplification of various numbers of input copies of HCV RNA in the presence of 50 µM spermine.

DEFINITIONS

To facilitate the understanding of this disclosure, the following definitions may be helpful.

As used herein, the term "polyamine" means an organic compound having more than one amino group or a salt of such compound. Polyamines include without limitation diamines, triamines, tetraamines and specifically, spermidine, spermine, putrescine, guanidine and diethylene triamine.

As used herein, the term "amplicon" means a population of DNA molecules that has been produced by amplification of a template, for example, by PCR.

As used herein, the term "target sequence" means a nucleic acid sequence of particular interest, possibly present in a sample.

As used herein, the term "abasic DNA" or "DNA with an abasic site" refers to a DNA molecule, either single stranded or double-stranded, that contains at least one abasic nucleotide sometimes called "abasic site". An "abasic nucleotide" is a nucleotide that lacks a base in the 1' position of the deoxyribose.

As used herein, the term "AP endonuclease" or "AP lyase" means an enzyme capable of breaking a phosphor-diester backbone of a nucleic acid at. The term includes the enzymes capable of breaking the backbone both 5' of the abasic site and 3' of the abasic site.

DETAILED DESCRIPTION OF THE INVENTION

The present invention involves an improved method of controlling carryover contamination of the nucleic acid amplification reactions using DNA glycosylases. As an example, the invention uses uracil-DNA glycosylase. The method generally starts with generating amplicons containing an unusual base. As an example, the invention uses uracil. This may be accomplished by performing nucleic acid amplification in the presence of dUTP, by incorporating deoxyuridine into the amplification primers or by deaminating cytosines in the DNA. After the first amplification reaction generates amplicons with uracil, any subsequent amplification reactions are pre-treated with an enzyme possessing a uracil-DNA glycosylase activity, for example, the UNG enzyme. If a contaminating amplicon from a prior amplification is present, UNG will cleave the uracil in such amplicon and generate an abasic site.

Although uracil and UNG are most commonly used to control contamination, it is noted that alternative enzyme/substrate systems that function in the same way are available. It is known in the art that specific DNA repair enzymes recognize and excise various unnatural bases from the DNA, leaving an abasic site. A combination of such unnatural base and a specific enzyme can be used to control carryover contamination as long as the polymerase is capable of incorporating the unnatural base into the potentially contaminating amplicon or, alternatively, the potentially contaminating amplicon can be treated in a way that results in the presence of the unnatural base. The examples of such enzyme/substrate pairs include MutY or MutM and 8-oxoguanosine, hOGG1 and 8-oxoguanosine, human MBD4 and uridine, E. coli Endo VIII and thymine glycol or other oxidized pyrimidines and a number of other similar pairs described, for example, in Hitomi et al. (2007) DNA Repair 6:410-428.

According to traditional methods, after incubation with UNG, the next step is subjecting the reaction mixture to thermal cycles. Amplification reactions, such as polymerase chain reaction (PCR) or ligation chain reaction (LCR), involve an initial heating or "denaturation step." It was believed that this initial heating step was sufficient to achieve degradation of the abasic DNA, because abasic DNA is known to be labile at high temperatures under high pH conditions. If the method failed to achieve sterilization, the practitioners suspected the failure of the enzymatic step with UNG. It is generally known that enzymes are sensitive to reaction conditions. At a slightest deviation from optimal conditions, an enzyme can lose a lot or all of its activity. Therefore an enzyme is often the first suspect when a method fails. On the other hand, non-enzymatic chemical reactions are thought to be more robust. For example, Kleiboeker ("Quantitative detection of the effect of uracil-DNA glycosylase on amplicon DNA degradation and RNA amplification in reverse transcription PCR", Virology Journal (2005) 2:29)) reports poor results with eliminating various templates. To improve the efficiency, Kleiboeker teaches increasing the amount of UNG, the time of incubation and increasing the incubation temperature. It is known however, that the presence of excessive amounts of UNG is detrimental to PCR. Although UNG is eventually inactivated by heat, it retains substantial activity for a long time during the thermocycles. As the temperature periodically nears the optimum of 50° C. (during the annealing step of PCR), UNG becomes partially active and starts digesting newly generated amplicons containing uracil. Therefore one may not keep adding ever greater amounts of UNG.

Surprisingly, the inventors discovered that UNG is not the cause of failures of the sterilization method. Contrary to expectations, the limiting factor in the sterilization method is not the enzymatic step, but the subsequent strand cleavage step. Having analyzed the intermediates of the UNG method by HPLC, the inventors determined that UNG converts over 95% of uracils in DNA into abasic sites. However, only 6% of the resulting abasic DNA is cleaved at 50° C. and only about 10% is cleaved at 95° C. Therefore inventors developed a useful improvement of the UNG sterilization method, involving addition of agents that facilitate degradation of the abasic DNA. Especially useful improvement involves the types of such agents that do not interfere with the subsequent amplification reactions.

In one embodiment, such agents are polyamines. Generally, polyamines are linear hydrocarbon molecules including, at a minimum, two amino groups, one amino group at each end. Some linear polyamines are substituted with non-linear or cyclical moieties. In addition to terminal amino groups, some polyamines also have one or more internal amino groups in the chain. In some embodiments, the polyamine has a structure where adjacent amino groups are separated from each other by three carbons. Comparative analysis of a large number of polyamines revealed that this structure enables optimal cleavage of abasic sites. See Steullet et al. "Cleavage of abasic sites in DNA by intercalator amines," Bioorg. Medic. Chem. 1999 (7), 2531-2540. This rule holds true regardless of the total number of atoms and of the total number of amino groups in the polyamine.

Examples of Useful Polyamines Include:
Spermidine, $(NH_2)(CH_2)_3(NH)(CH_2)_4(NH_2)$;
Spermine, $(NH_2)(CH_2)_3(NH)(CH_2)_4(NH)(CH_2)_3(NH_2)$; and
Trimethylenediamine, $(NH_2)(CH_2)_3(NH_2)$.

In some embodiments the polyamine is an intercalator amine. Polyamines of this group possess an intercalating moiety, capable of intercalating between the base pairs or bases in a nucleic acid. Examples of intercalating moieties on a polyamine include arenes and polyarenes, such as naphthalene and anthraquinone. In some embodiments, the intercalator moiety itself may also be substituted with one or more polyamine side chains. Intercalator amines are often more efficient at degrading abasic nucleic acids than the linear amines. Without being bound by a particular theory, one may suggest that this effect is likely due to intercalation, which brings the active part of the polyamine molecule into proximity with its target abasic site.

Polyamines are known to improve the efficiency of various enzymatic reactions involving nucleic acids. For example, it has been discovered that polyamines (ethylenediamine, thrimethylenediamine, spermidine and spermine) sometimes improve the efficiency of PCR amplification using impure samples, such as blood and plant or animal tissue. (See English-language abstracts of Japanese application publications JP11113573, JP2001008680, JP8009997 and JP6277061). Generally, various polyamines were found to be very similar in their ability to assist enzymatic reactions. U.S. Pat. No. 6,413,747 "Enhancement of nucleic acid amplification by the addition of a polyamine" discloses the use of nine different polyamines, each of which was able to increase the efficiency of PCR. Another group found that polyamines increase the efficiency while decreasing specificity of the PCR using DNA extracted from frozen barley seeds. See Ahokas H. and M. J. Erkkila "Interference of PCR amplification by the polyamines, spermine and spermidine", (1993) PCR Methods Appl., 3:65-68. This group found that increasing concentration of polyamines in the reaction from 0.6 mM to 0.8 mM results in four additional PCR products from the same template-primer combination.

Without being bound by a particular theory, one may suggest that taken together, the existing data shows that polyamines improve amplification of damaged DNA. It is possible that polyamines enhance the polymerase's ability to bypass the sites of DNA damage, such as abasic sites. Following this logic, one would expect that, in the same way, polyamines would allow amplification of UNG-digested contaminants before they are degraded during PCR. Thus one would conclude that polyamines would counteract the UNG-based method of preventing carryover contamination and should not be used in conjunction with this method. On the contrary, it has been discovered that polyamines actually improve the UNG-based contamination control by enhancing degradation of DNA at the abasic sites.

It is understood that the success of removing a carryover contaminant is related to the base composition of the amplicon to be eliminated. Low deoxyadenosine content of the strand to be copied leads to low deoxyuridine content in the amplification product, made in the presence of dUTP. Therefore after UNG treatment, such amplification product would have the fewest abasic sites and undergo the least breakages of the backbone. It is further understood, that if uridines are distributed asymmetrically between the two strands of an amplicon, the uridine-poor strand may survive the sterilization procedure and ensure survival of the entire contaminating amplicon. In the Examples below, targets with different numbers and proportions of thymidines were used. As shown in Table 1, the dT (dU) content of the target strands ranged from 15% to 35%. Target sequence Target 2 was selected for the Examples described below. This target sequence has the lowest absolute number of thymidines (66) in a double stranded form as well as the lowest absolute and relative thymidine content in a single strand (the forward strand).

TABLE 1

| dT (dU) content of various target sequences | | | | | | |
|---|---|---|---|---|---|---|
| Target | Target 1 | Target 2 | Target 3 | Target 4 | Target 5 | Internal Control |
| Size, bp | 154 | 141 | 157 | 132 | 241 | 124 |
| Total dTs | 79 (25%) | 66 (23%) | 79 (25%) | 72 (27%) | 95 (20%) | 61 (25%) |

TABLE 1-continued dT (dU) content of various target sequences

| Target | Target 1 | Target 2 | Target 3 | Target 4 | Target 5 | Internal Control |
|---|---|---|---|---|---|---|
| Fwd strand dTs | 32 (21%) | 22 (15%) | 47 (30%) | 46 (35%) | 51 (21%) | 32 (26%) |
| Rev strand dTs | 47 (31%) | 44 (31%) | 32 (20%) | 26 (20%) | 44 (18%) | 29 (23%) |

While replacing all thymidines with uracils assures maximum activity of UNG on an amplicon, it may be desirable to generate amplicons with a mixture of thymidines and uracils. This is because many DNA polymerases known in the art have lower preference for dUTP as a substrate. As shown in Examples below, amplification in the presence of dUTP alone is generally less efficient than amplification in the presence of both dUTP and dTTP. It is understood that the difference in efficiency may vary among different target sequences and with the amounts of dTTP and dUTP in the reaction mixture. Therefore for some target sequences, adding various amounts of dTTP to the reaction mixture may be recommended. In some embodiments, the molar ratio dTTP:dUTP in the amplification reaction is 1:10. In some embodiments, the concentration of dUTP is higher than that of dATP, dCTP and dGTP. In one example, the concentrations of nucleotides in the amplification reaction may be 0.3 mM of each dATP, dCTP and dGTP, 0.5 mM dUTP and 0.05 mM dTTP.

In other examples, the agents that facilitate degradation of the abasic DNA are enzymes such as endonuclease IV, exonuclease III or AP lyase.

Kits

The present invention also provides kits useful for employing the method of the invention. The kits comprise one or more reagents described herein. Optionally, the kits can include paper or electronic instructions.

In some examples, the kits would include a polyamine suitable for aiding in non-enzymatic degradation of abasic DNA. In other examples, the kits would include an enzyme capable of degrading the abasic DNA. Other reagents in the kit may include the reagents useful for amplification of nucleic acids. These reagents include, without limitation, one or more oligonucleotide primers, nucleic acid polymerase, buffers, salts and nucleoside triphosphates and an enzyme with DNA glycosylase activity, such as uracil-N-glycosylase activity. The nucleoside triphosphates include dATP, dCTP, dGTP and one or more of dUTP and dTTP. Instead of dUTP, another suitable unconventional nucleoside triphosphate may be added. If another unconventional nucleoside triphosphate is used, the composition of the conventional nucleoside triphosphates may be altered accordingly. Additional reagents in the kit can be reagents useful for detection of the amplified nucleic acids. These reagents include, without limitation, one or more labeled probes, such as radioactively or fluorescently labeled probes, TaqMan™ probes and other real-time PCR probes.

Reaction Mixtures

The present invention also provides reaction mixtures. A typical reaction mixture will comprise the components used for amplification of nucleic acids, and one or more reagents to facilitate the generation and degradation of abasic DNA. In some embodiments, the reaction mixtures will contain the reagents used for the detection of nucleic acids. In some embodiments, the reaction mixtures will contain reagents used to prevent further carryover contamination. An exemplary reaction mixture would comprise one or more oligonucleotide primers, nucleic acid polymerase, buffers, salts, nucleoside triphosphates, and an enzyme with DNA glycosylase activity, such as uracil-N-glycosylase activity. In some embodiments, the reaction mixtures will further contain a polyamine. In some embodiments, the reaction mixtures will further contain an enzyme capable of cleaving abasic DNA. In some embodiments, the reaction mixtures will further contain one or more labeled probes.

It is noted, that the scope of the present invention includes any amplification method which is susceptible to carryover contamination. The amplification methods include, without limitation, polymerase chain reaction (PCR), real-time PCR, end-point PCR, asymmetric PCR and ligation chain reaction (LCR).

EXAMPLES

The following examples illustrate the method of the present invention.

Example 1

Figure 1A:
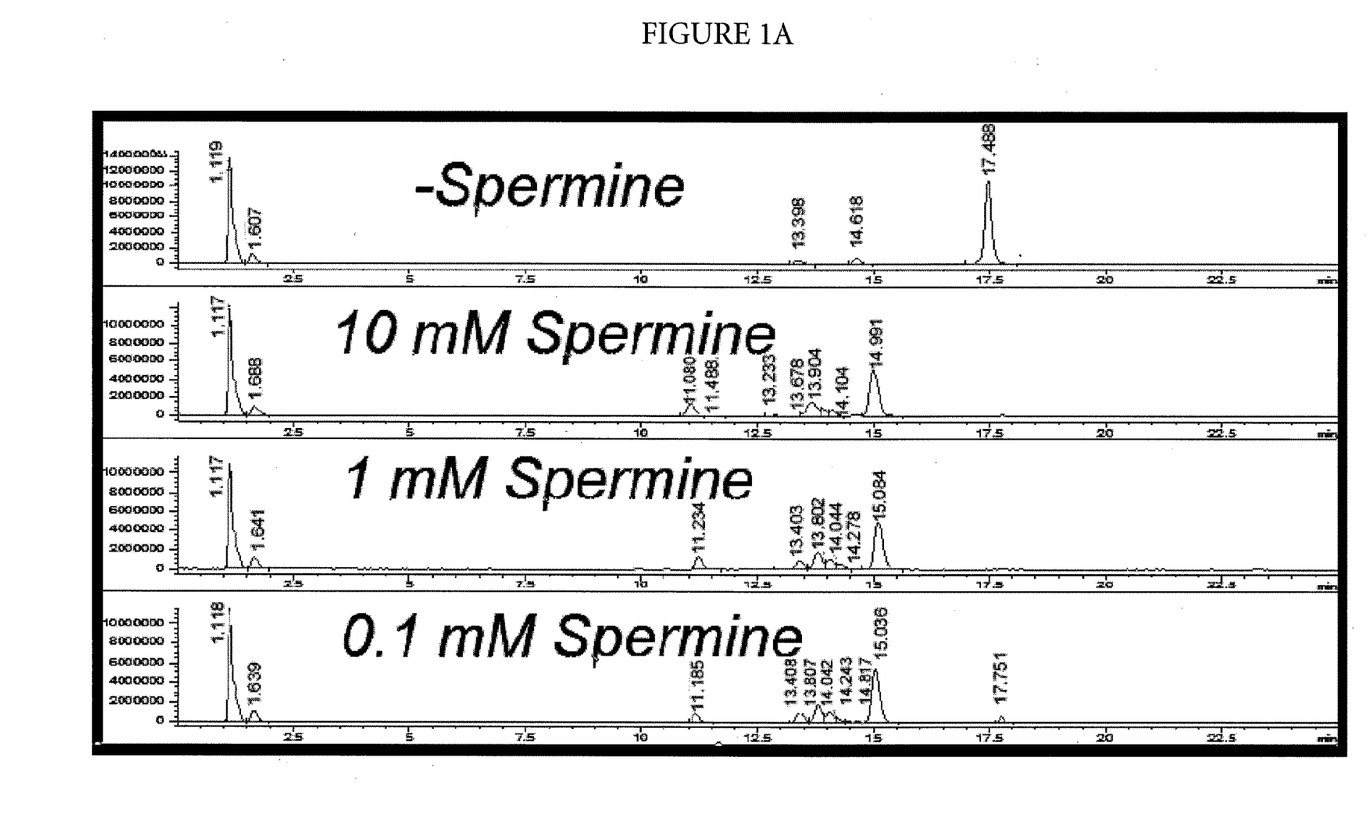
FIGS. 1A and B show HPLC chromatograms of degradation products of an oligonucleotide having abasic sites, in the absence or presence of increasing concentrations of spermine.
Figure 1B:
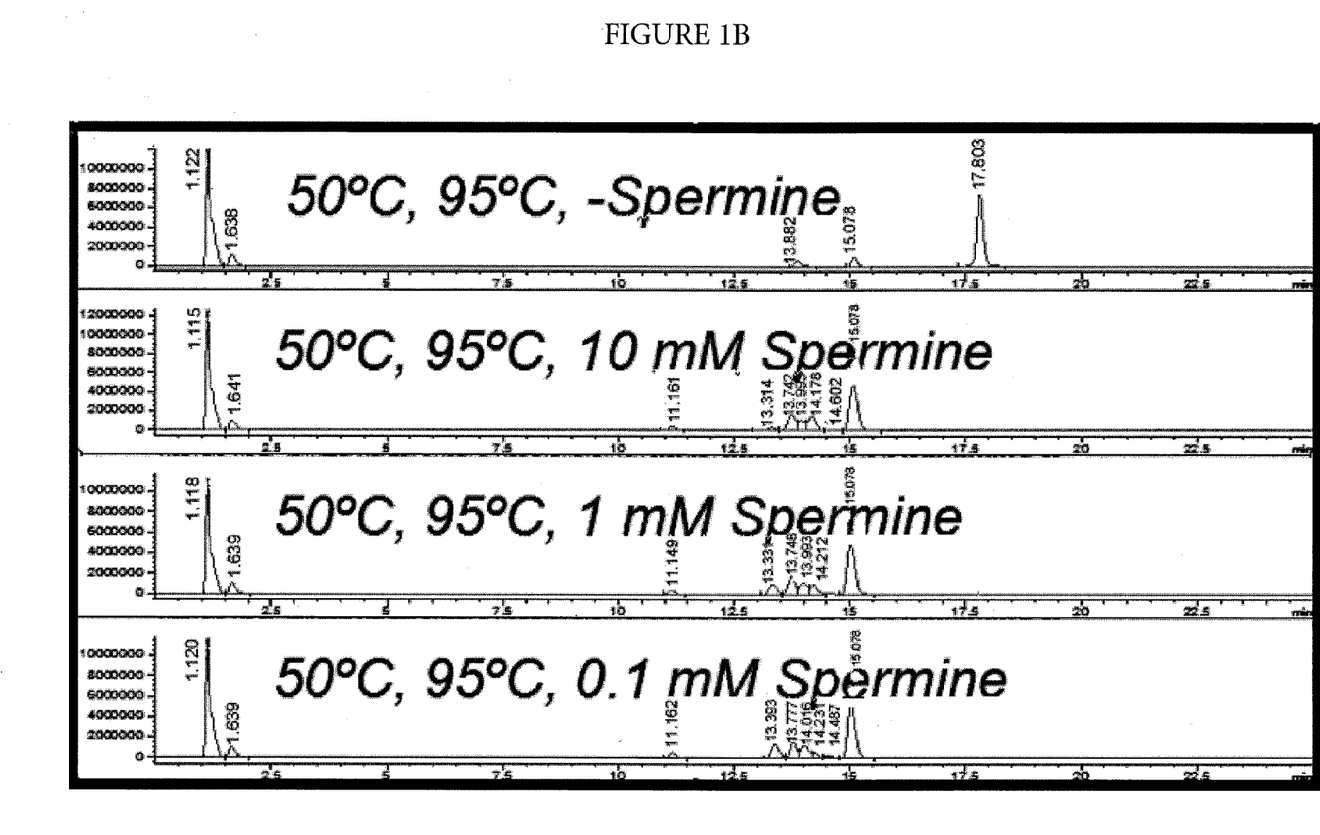

Effect of Spermine on Degradation of an Oligonucleotide Having Abasic Sites The deoxyuracil-containing DNA oligonucleotide of SEQ ID NO: 1:

5'-TTTGCATGGCTGC<u>U</u>TGATGTCCCCCCACT-3' was incubated in a solution prepared by combining a 10 µL aliquot of a 100 µM solution with 10 µL of a mock RT-PCR mastermix solution. The mock mastermix solution contained 50-mM tricine (pH 8.3), 90 mM potassium acetate, 200 µM each of dATP, dCTP and dGTP, 400 µM dUTP, 4 mM manganese acetate, 5% DMSO, and 5% glycerol. Additionally, the reaction mixture contained 2.5 µL of water or spermine solution at the appropriate concentration, and 2 µL of 4 units/µL UNG. The incubations were for 30 minutes at 50° C., with or without a further heat spike step at 95° C. for two minutes. The reactions were analyzed by HPLC-MS using an Agilent 1100 MSD detection system with an electrospray ionization source. The mass-spectrometry (MS) data (not shown) clearly showed that under all conditions, the removal of uracil was complete (to the limits of the detection method). The HPLC results are shown on FIGS. 1A and 1B. FIG. 1A shows degradation at 50° C. in the presence of 100 µM, 1 mM and 10 mM spermine. At 100 µM, the full-length oligonucleotide is still detectable. FIG. 1B shows degradation after a 2-minute exposure to 95° C., also in the presence of 100 µM, 1 mM and 10 mM spermine. At 95° C., even at 100 µM, the full-length oligonucleotide is no longer detectable. The results illustrate that with the increasing amount of spermine, the full-length oligonucleotide is being more efficiently degraded into fragments. At higher temperatures, the effect is achieved with lower concentration of spermine. However, as the results show, higher temperatures alone are insufficient to cause degradation of the abasic DNA.

Example 2

Amplification of DNA and RNA in the Presence of Spermine

Figure 2A:
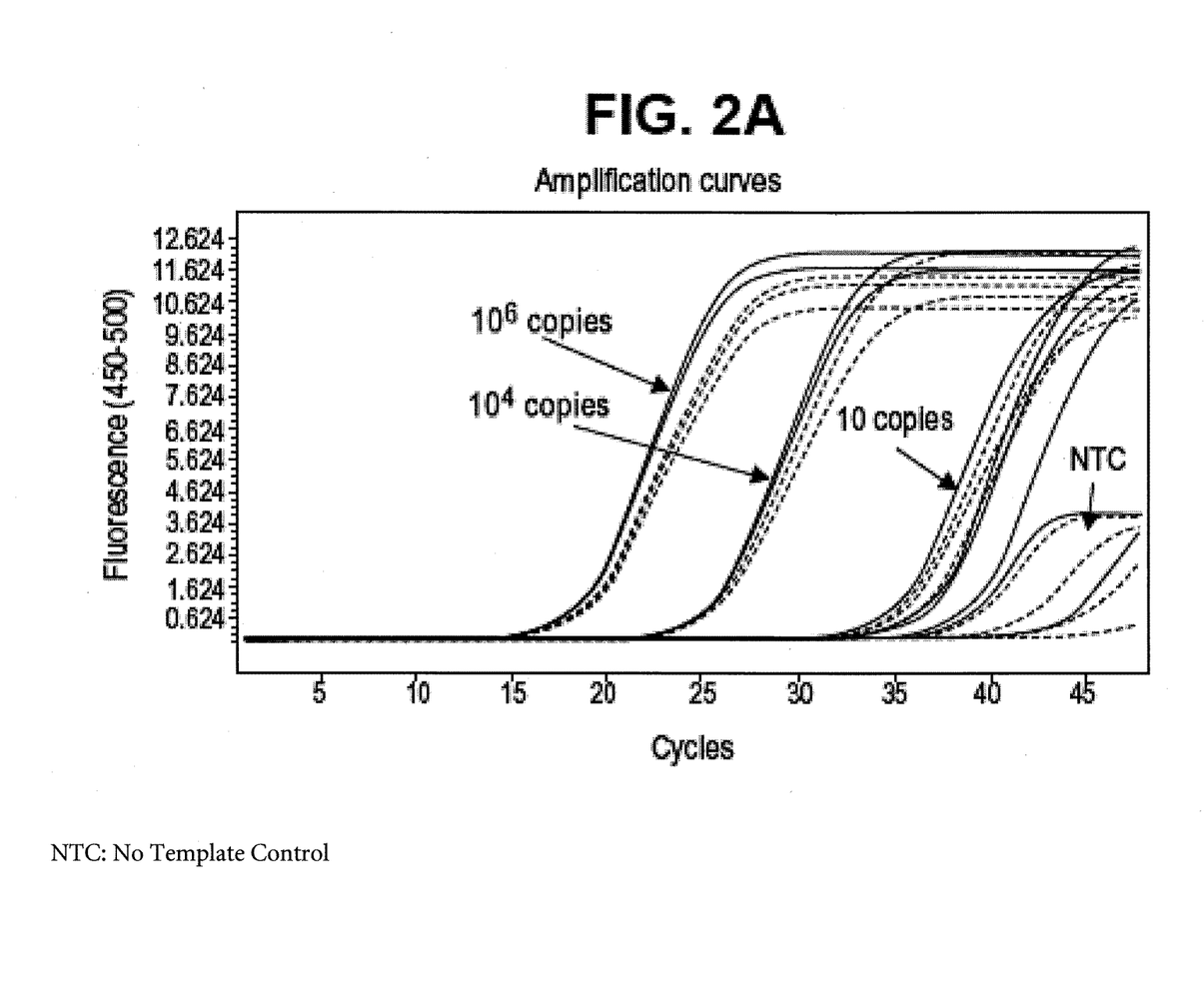
FIGS. 2A and B show the results of amplification of various amounts of DNA and RNA targets in the absence or presence of spermine.

For DNA, a polymerase chain reaction was performed to amplify a 241-bp DNA template (Target 5, 20% dT for double-stranded DNA). The reaction mixture contained 40 units of ZO5 DNA polymerase, 50 mM tricine (pH 8.3), 90 mM potassium acetate, 200 µM each of dATP, dCTP and dGTP, 400 µM dUTP, 0.1 µM of each upstream and downstream primers, 4 mM manganese acetate, 5% DMSO, and 5% glycerol, 2 µM SYTO-16 intercalating dye, and optionally, 100 µM spermine. Amplification was performed in a Roche LightCycler 480 instrument using the following temperature profile 50° C. for 5 min (UNG step), two cycles of 94° C. for 15 sec (denaturation) and 59° C. for 40 sec (annealing and extension), 48 cycles of 91° C. (denaturation) and 59° C. for 40 sec (annealing and extension). The fluorescence data was collected during the anneal/extend steps of the last 48 cycles using a 483 nm/533 nm filter combination for excitation and emission respectively. Results are shown in FIG. 2A, and Table 2A. The clusters of solid lines represent amplification reactions without spermine, done in triplicate. The clusters of dashed lines represent amplification reactions in the presence spermine, done in triplicate. The results illustrate that amplification is not significantly inhibited by spermine.

TABLE 2A

PCR amplification of DNA (Ct values) in the presence or absence of spermine

| Template copy # | No spermine | 100 µM spermine | Ct difference |
| --- | --- | --- | --- |
| $10^6$ | 18.8 | 19.0 | +0.2 |
| $10^4$ | 25.7 | 25.9 | +0.2 |
| 10 | 36.6 | 36.1 | −0.5 |

Figure 2B:
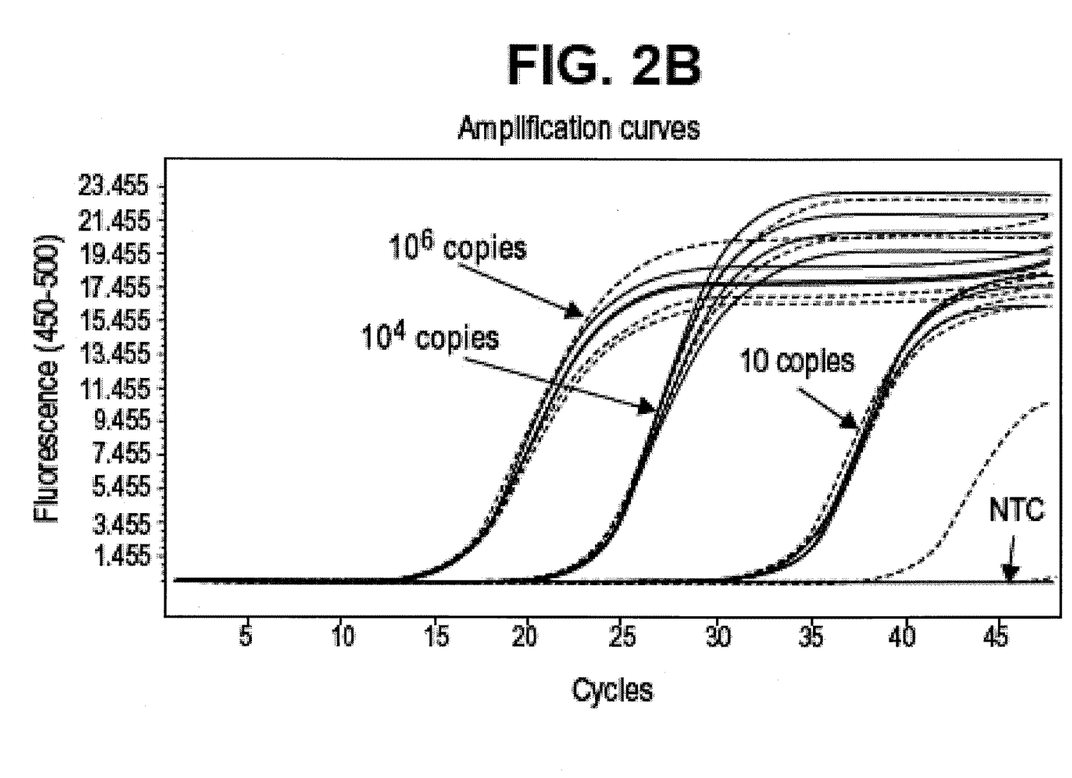

For RNA, a reverse transcription polymerase chain reaction (RT-PCR) was performed to amplify 0-$10^6$ copies of an RNA equivalent of Target 5. The reaction mixture and temperature profile were the same as for the DNA template, except reverse transcriptase was added and after the initial UNG step, the reaction was incubated at 66° C. for 30 min (reverse transcription). Results are shown in FIG. 2B, and Table 2B. As on FIG. 2A, the clusters of solid lines represent amplification reactions without spermine, done in triplicate. The clusters of dashed lines represent amplification reactions in the presence spermine, done in triplicate. The results illustrate that RT-PCR is not significantly inhibited by spermine.

TABLE 2B

Amplification (avg. Ct values) of 10, $10^4$, or $10^6$ copies of an RNA target in the absence or presence 100 µM spermine.

| Copy Number | no Spermine | with Spermine | Ct difference |
| --- | --- | --- | --- |
| 10 | 34.4 | 34.0 | −0.3 |
| $10^4$ | 23.8 | 23.5 | −0.3 |
| $10^6$ | 16.8 | 16.6 | −0.2 |

Example 3

Figure 3:
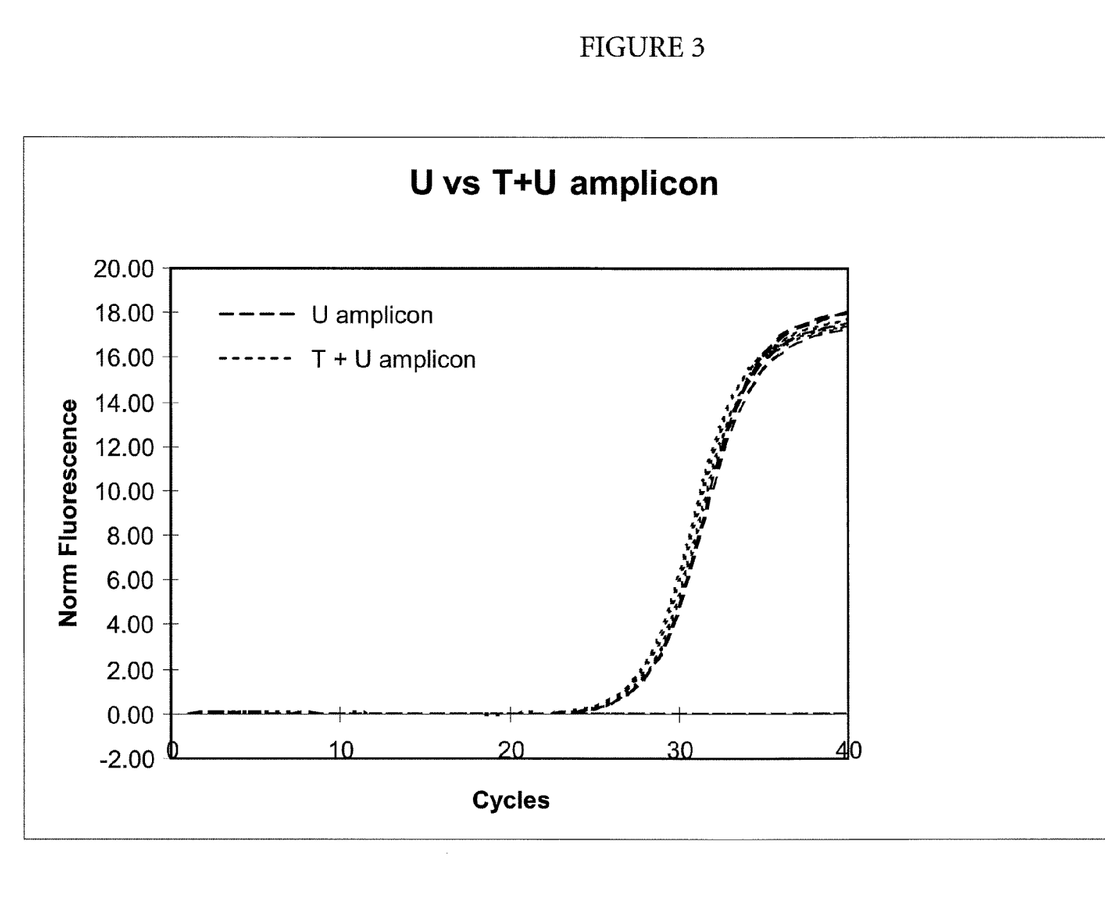
FIG. 3 shows the results of amplification of a target sequence using either dUTP alone or a combination of dUTP and dTTP.

Efficiency of Amplification in the Presence of dUTP Only or a Combination of dUTP and dTTP A reverse transcription polymerase chain reaction (RT-PCR) was performed to amplify 100,000 copies of a 141-nt RNA template (Target 2 from Table 1). This target has a very low dU content. The corresponding double-stranded DNA has 23% dT (Table 1). When the amplification is conducted in the presence of both dTTP and dUTP, the dU content of the DNA amplicon would be even lower. The reaction mixture included 0.5 M betaine, pH 6.3; 68 mM potassium acetate, pH 7.0; 2.8% glycerol; 3 mM manganese acetate, pH 6.1; 0.07% sodium azide; 5% DMSO; 50 mM tricine, pH 8.3; 0.3 mM each dATP, dCTP and dGTP; 0.5 mM dUTP; and where indicated, 0.05 mM dTTP; 40 units ZO5 DNA polymerase; 0.2 µM aptamer 0.2 µM each forward and reverse primer and 0.1 µM probe. The temperature profile was: 94° C. for 30 sec, 58° C. for 30 min (reverse transcription), five cycles of 95° C. for 15 sec and 59° C. for 21 sec, further 52 cycles of 91° C. for 15 sec and 52° C. for 33 sec, followed by 72° C. for 5 min and final 40° C. for 2 min. The results are shown on FIG. 3 and Table 3. In this experiment, amplification in the presence of dUTP is approximately as efficient as amplification in the presence of both dUTP and dTTP.

TABLE 3

Amplification (Ct values) of the 100,000 copies of Target 2 in the presence of dUTP alone or a mixture of dUTP and dTTP

|  | dUTP | dUTP + dTTP |
| --- | --- | --- |
| Average* Ct | 26.2 | 25.9 |
| Std deviation | 0.05 | 0.2 |

*average of five tests

Example 4

Effect of Increasing Concentrations of UNG on a dT(dU)-Poor Amplicon

Figure 4:
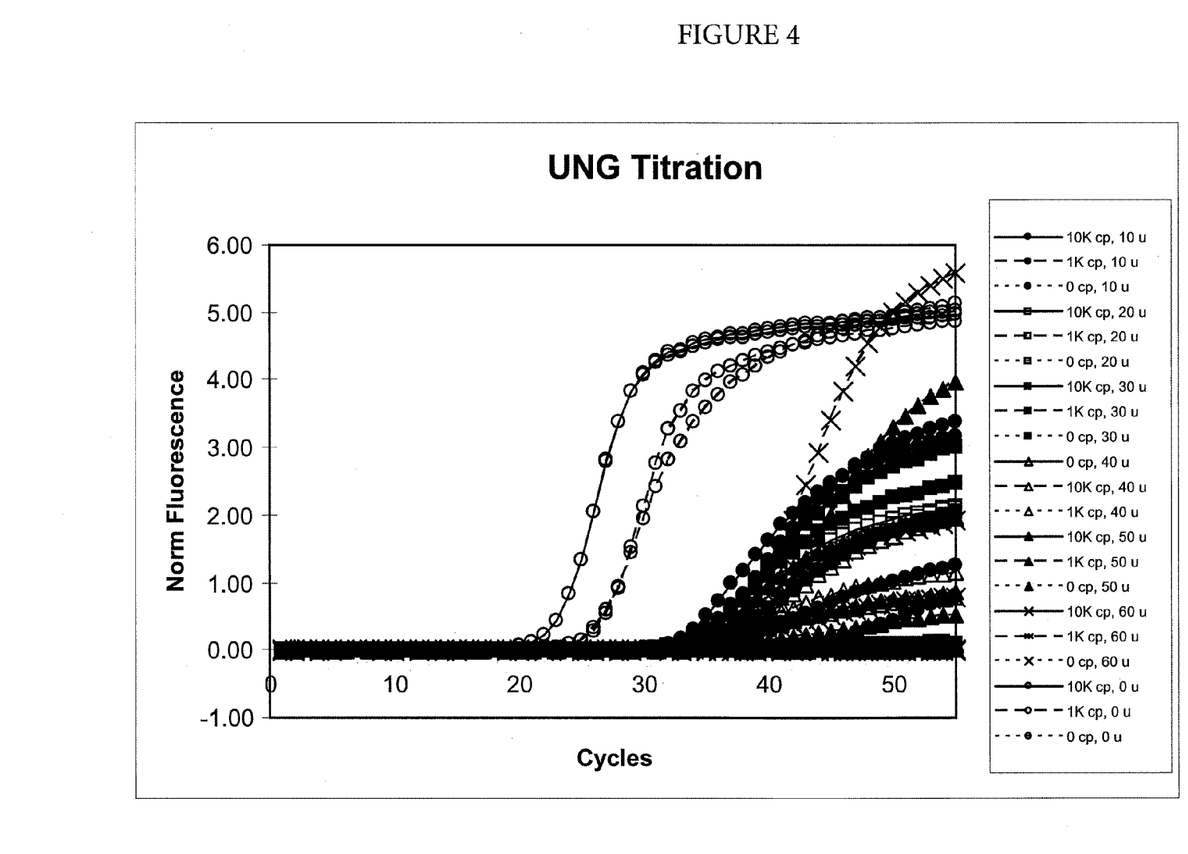
FIG. 4 shows the results of amplification after pre-treatment with increasing amounts of UNG.

In this example, the amplicon of Target 2, generated using a nucleotide mixture containing 0.5 mM dUTP and 0.05 mM TTP, as described in example 3 was used as the target for amplification (23% total dU+T). The amplicon was purified using the QIAQUICK® PCR purification kit (Qiagen, Valencia, Calif.) and quantified by spectrophotometry. The amplifications were performed with 1000, or 10,000 copies of the amplicon spiked into human plasma from healthy donors, processed with the COBAS AmpliPrep instrument (Roche Molecular Systems, Pleasanton, Calif.). The reactions were performed in the absence, or in the presence of increasing amounts of UNG. The RT-PCR amplification was performed with the primer and target sequences, reagents and temperature profile described in Example 3, except the indicated amount of UNG was added. Amplification and detection were performed in a COBAS TaqMan® instrument, using the following temperature profile: 50° C. for 2 min (UNG step), 94° C. for 30 sec, 58° C. for 30 min (RT step), 5 cycles of 95° C. for 15 sec (denaturation) and 59° C. for 21 sec (annealing and extension), 55 cycles of 91° C. for 15 sec (denaturation) and 52° C. for 33 sec (annealing and extension. The results are shown in FIG. 4 and Table 4. As the data in FIG. 4, and Table 4 shows, the dU-poor amplicon survived the treatment with even 60 units/100 µL of UNG (six times the recommended amount).

TABLE 4

Amplification of 10,000 copies of a dT(dU)-poor amplicon after pre-treatment with increasing amounts of UNG

| No UNG | 10u UNG | 20u UNG | 30u UNG | 40u UNG | 50u UNG | 60u UNG |
|---|---|---|---|---|---|---|
| 23.2* | 35.6 | 37.3 | 36.6 | 41.9 | 40.0 | 41.6 |

*each value is an average of two separate experiments

Example 5

Figure 5:
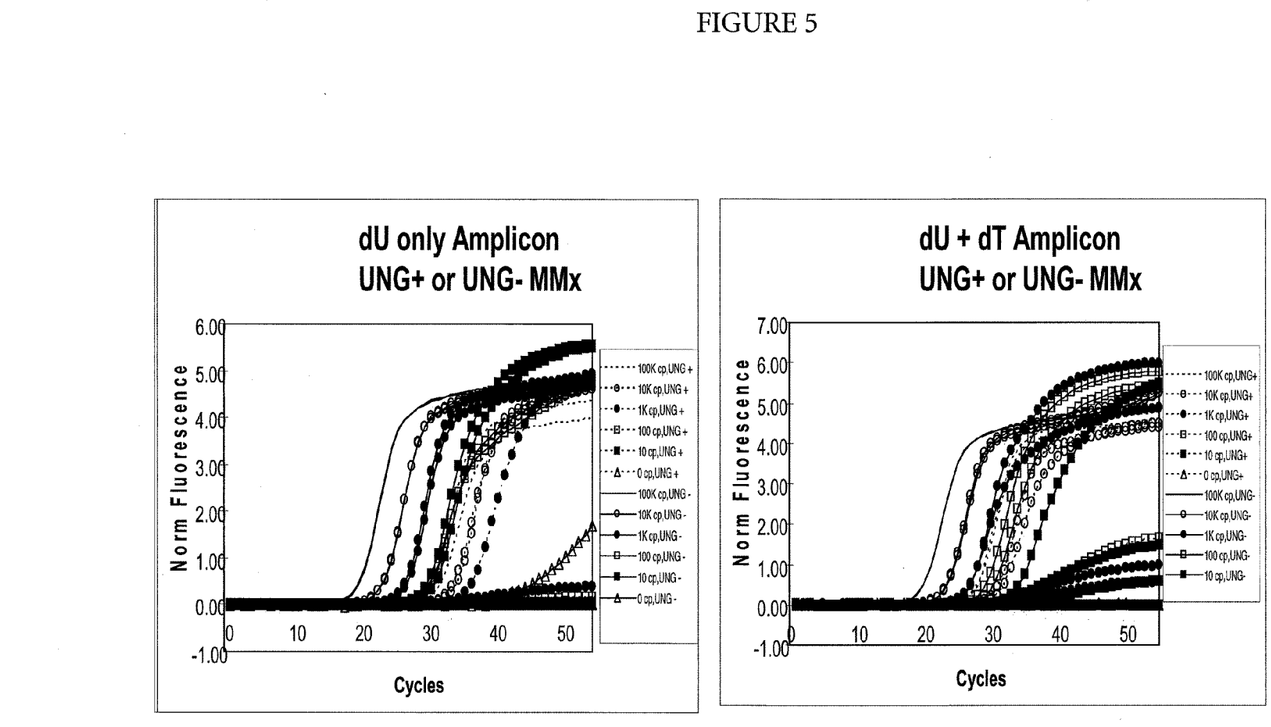
FIG. 5 shows the results of amplification of dU and dU/dT containing sequences with or without pre-treatment with UNG.

Amplification of Sequences Containing Both dU and dT after Pretreatment with UNG In this example, pre-treatment with UNG and real-time RT-PCR amplification were performed as described in Example 4. Results are shown in FIG. 5 and Table 5. The results demonstrate that the amplicon with both dT and dU is more persistent, i.e. harder to eliminate than the amplicon containing only dU.

TABLE 5

Amplification of dU and dT + dU-containing sequences with and without pre-treatment with UNG

| Amplicon copy number added | Amplicon with only dU +UNG | Amplicon with only dU No UNG | Amplicon with dT and dU +UNG | Amplicon with dT and dU No UNG |
|---|---|---|---|---|
| 100,000 | 31.8* | 20.3 | 28.0 | 19.9 |
| 10,000 | 34.5 | 23.9 | 31.5 | 23.4 |
| 1,000 | 37.2** | 27.3 | 43.7 | 27.0 |
| 100 | ND*** | 31.1 | 39.7** | 29.7 |
| 10 | ND | ND | 49.7** | 35.9 |

*each value is an average of two separate experiments
**represents a single value, the other one of the two experiments had an ND result
***ND—not detected

Example 6

Amplification after Pre-Treatment with UNG and in the Presence of Spermine

Figure 6:
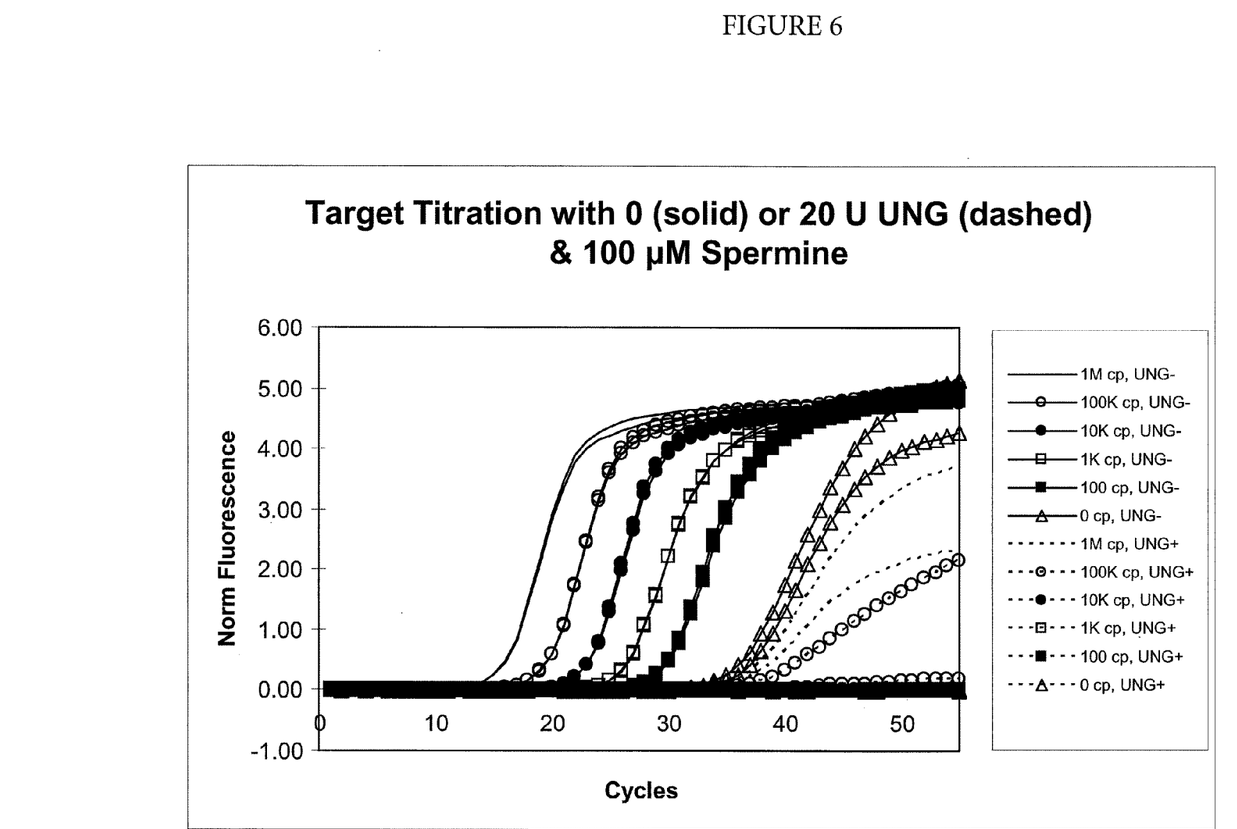
FIG. 6 shows the results of amplification after pre-treatment with UNG in the presence of spermine.

In this example, a target containing both dT and dU was amplified after pretreatment with UNG as described in Example 4, except the amplification reaction mixture also contained 100 μM spermine. The results are shown in FIG. 6 and Table 6. As compared to Table 5, the data show a 1,000-fold or more improvement in controlling contamination.

TABLE 6

Amplification of a dT + dU-containing sequences after pre-treatment with UNG and in the presence of 100 μM spermine

| Amplicon copy number added | No UNG | 20u UNG |
|---|---|---|
| 1,000,000 | 16.1* | 38.7 |
| 100,000 | 19.7 | 41.4** |
| 10,000 | 23.3 | ND*** |
| 1,000 | 26.7 | ND |
| 100 | 30 | ND |

*each value is an average of two separate experiments
**represents a single value, the other one of the two experiments had an ND result
***ND—not detected

Example 7

Figure 7:
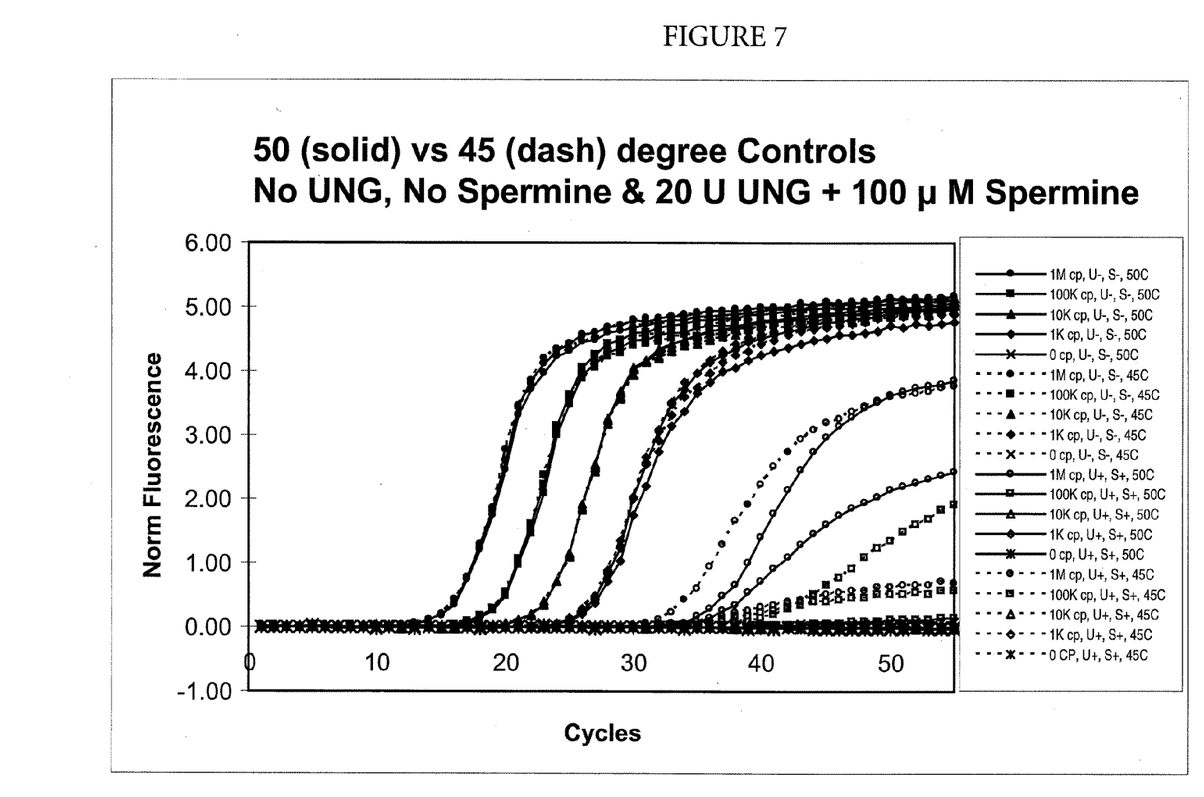
FIG. 7 shows the results of amplification after pre-treatment with UNG at various temperatures.

Amplification after Pre-Treatment with UNG at Various Temperatures in the Presence of Spermine In this example, amplification of the target containing both dT and dU was performed as described in Example 6, except pre-treatment with UNG was conducted either at 45° C. or at 50° C. The control reaction contained no UNG and no spermine. The test reaction contained both UNG and spermine. The results are shown on FIG. 7 and in Table 7. In this experiment, the method performs better at 50° C. than at 45° C.

TABLE 7

Amplification of a dT and dU-containing sequences after pre-treatment with UNG at 50° C. and 45° C.

| | 50° C. | | 45° C. | |
|---|---|---|---|---|
| Amplicon copy number added | No UNG No spermine | 20u UNG 100 μM spermine | No UNG No spermine | 20u UNG 100 μM spermine |
| 1,000,000 | 16.4* | 38.0 | 16.2 | 39.7 |
| 100,000 | 20.0 | ND*** | 19.8 | 46.5 |
| 10,000 | 23.4 | ND | 23.3 | ND |
| 1,000 | 27.1 | ND | 27.1 | ND |

*each value is an average of two separate experiments
***ND—not detected

While the invention has been described in detail with reference to specific examples, it will be apparent to one skilled in the art that various modifications can be made within the scope of this invention. Thus the scope of the invention should not be limited by any of the examples described herein, but by the claims presented below.

What is claimed is:

1. A method of reducing carryover contamination during amplification by polymerase chain reaction (PCR) of a nucleic acid, comprising the steps of:
   a. providing a sample solution containing said nucleic acid;
   b. amplifying said nucleic acid in the presence of an enzyme possessing DNA glycosylase activity to generate DNA with at least one abasic site;
   c. providing at least one reagent facilitating degradation of abasic DNA wherein said reagent is a polyamine;
   d. incubating said sample solution at the conditions suitable to cause degradation of said DNA with at least one abasic site.

2. The method of claim 1, wherein said DNA glycosylase activity is uracil-N-DNA glycosylase activity.

3. The method of claim 1, wherein said polyamine is an intercalator polyamine.

4. The method of claim 1, wherein said polyamine is selected from a group consisting of spermidine, spermine, triethylenetetramine, and trimethylenediamine.

5. The method of claim 1, wherein said polyamine is added at the concentration between 0.01 mM and 1 mM.

6. The method of claim 1, wherein said conditions in step d) are characterized by temperature in the range between 30° C. and 95° C.

* * * * *